United States Patent
Bantz et al.

(10) Patent No.: US 9,153,135 B2
(45) Date of Patent: Oct. 6, 2015

(54) MOBILE COMPUTING DEVICE EMERGENCY WARNING SYSTEM AND METHOD

(75) Inventors: David F. Bantz, Portland, MA (US);
Thomas E. Chefalas, Somers, NY (US);
Leslie S. Liu, White Plains, NY (US);
Steven J. Mastrianni, Unionville, CT (US); James R. Moulic, Poughkeepsie, NY (US); Dennis G. Shea, Ridgefield, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 13/602,866

(22) Filed: Sep. 4, 2012

(65) Prior Publication Data

US 2012/0326860 A1   Dec. 27, 2012

Related U.S. Application Data

(63) Continuation of application No. 13/004,462, filed on Jan. 11, 2011.

(51) Int. Cl.
| | |
|---|---|
| *G08B 1/08* | (2006.01) |
| *G08G 1/00* | (2006.01) |
| *G08G 1/0967* | (2006.01) |
| *G08G 1/16* | (2006.01) |
| *A61B 5/00* | (2006.01) |
| *G06F 19/00* | (2011.01) |

(52) U.S. Cl.
CPC .......... *G08G 1/205* (2013.01); *G08G 1/096741* (2013.01); *G08G 1/096775* (2013.01); *G08G 1/16* (2013.01); *A61B 5/0002* (2013.01); *A61B 5/0022* (2013.01); *A61B 5/747* (2013.01); *G06F 19/3418* (2013.01)

(58) Field of Classification Search
CPC ............ B60N 2/002; B60Q 9/00; G08G 1/04; G08G 1/0967
USPC .......... 340/572.1, 539.1, 539.11, 539.12, 903
See application file for complete search history.

(56) References Cited

U.S. PATENT DOCUMENTS

| | | | | |
|---|---|---|---|---|
| 5,081,667 | A * | 1/1992 | Drori et al. ................. | 455/404.1 |
| 5,103,474 | A * | 4/1992 | Stoodley et al. ............. | 455/403 |
| 5,218,367 | A * | 6/1993 | Sheffer et al. ................ | 342/457 |
| 5,482,314 | A * | 1/1996 | Corrado et al. .............. | 280/735 |
| 6,049,711 | A * | 4/2000 | Ben-Yehezkel et al. ... | 455/414.3 |

(Continued)

OTHER PUBLICATIONS

Office Action dated Jan. 3, 2013 for U.S. Appl. No. 13/603,585.

(Continued)

*Primary Examiner* — Jennifer Mehmood
*Assistant Examiner* — Rufus Point
(74) *Attorney, Agent, or Firm* — Tutunjian & Bitetto, P.C.; Louis J. Percello

(57) ABSTRACT

A warning system and method include a memory device configured to store one or more condition criteria. A monitoring device is configured to monitor a status of the one or more condition criteria. The monitoring device is triggered by a triggering event related to the status to generate a warning signal responsive to the triggering event. A mobile computing device is configured to communicate with the monitoring device and an external network to receive the warning signal and output a warning message on the external network to one or more designated entities.

19 Claims, 3 Drawing Sheets

(56) References Cited

U.S. PATENT DOCUMENTS

| | | | |
|---|---|---|---|
| 6,184,801 B1* | 2/2001 | Janky | 340/988 |
| 6,337,641 B1* | 1/2002 | Yoshioka et al. | 340/989 |
| 6,405,213 B1* | 6/2002 | Layson et al. | 707/758 |
| 6,526,352 B1* | 2/2003 | Breed et al. | 701/470 |
| 6,529,723 B1* | 3/2003 | Bentley | 455/405 |
| 6,535,743 B1* | 3/2003 | Kennedy et al. | 455/456.1 |
| 6,553,262 B1* | 4/2003 | Lang et al. | 607/32 |
| 6,603,405 B2* | 8/2003 | Smith | 340/905 |
| 6,674,362 B2* | 1/2004 | Yoshioka et al. | 340/506 |
| 6,690,302 B1* | 2/2004 | Inomata | 340/989 |
| 6,694,234 B2* | 2/2004 | Lockwood et al. | 701/31.5 |
| 6,728,605 B2* | 4/2004 | Lash et al. | 701/1 |
| 6,847,889 B2* | 1/2005 | Park et al. | 701/420 |
| 7,023,332 B2* | 4/2006 | Saito et al. | 340/438 |
| 7,221,928 B2* | 5/2007 | Laird et al. | 455/404.1 |
| 7,515,066 B2* | 4/2009 | Watanabe | 340/903 |
| 7,639,148 B2 | 12/2009 | Victor | |
| 7,876,205 B2* | 1/2011 | Catten et al. | 340/439 |
| 7,893,818 B2* | 2/2011 | Smoyer et al. | 340/426.12 |
| 8,005,490 B2* | 8/2011 | Miyake | 455/456.4 |
| 8,098,132 B2* | 1/2012 | Scalisi et al. | 340/7.21 |
| 8,290,480 B2 | 10/2012 | Abramson et al. | |
| 8,396,002 B2* | 3/2013 | Marshall-Wilson | 370/252 |
| 2001/0040504 A1* | 11/2001 | Gehlot | 340/426 |
| 2001/0040506 A1* | 11/2001 | Boulay et al. | 340/539 |
| 2002/0044049 A1* | 4/2002 | Saito et al. | 340/438 |
| 2002/0161495 A1* | 10/2002 | Yamaki | 701/33 |
| 2002/0173881 A1* | 11/2002 | Lash et al. | 701/1 |
| 2002/0198660 A1* | 12/2002 | Lutter et al. | 701/301 |
| 2003/0009270 A1* | 1/2003 | Breed | 701/29 |
| 2003/0095038 A1* | 5/2003 | Dix | 340/425.5 |
| 2003/0128123 A1* | 7/2003 | Sumiya et al. | 340/573.1 |
| 2003/0212480 A1* | 11/2003 | Lutter et al. | 701/33 |
| 2005/0033504 A1* | 2/2005 | Rennels | 701/117 |
| 2005/0071085 A1* | 3/2005 | Root et al. | 702/3 |
| 2005/0162284 A1* | 7/2005 | Hanebrink | 340/995.13 |
| 2005/0179518 A1* | 8/2005 | Kawamura et al. | 340/5.23 |
| 2005/0203698 A1* | 9/2005 | Lee | 701/200 |
| 2005/0222730 A1 | 10/2005 | Taipale | |
| 2005/0222752 A1* | 10/2005 | Sokola et al. | 701/200 |
| 2006/0020380 A1* | 1/2006 | Saito et al. | 701/29 |
| 2006/0059364 A1* | 3/2006 | Fontijn | 713/186 |
| 2007/0135978 A1* | 6/2007 | Kim et al. | 701/29 |
| 2007/0156311 A1* | 7/2007 | Elcock et al. | 701/29 |
| 2008/0122595 A1* | 5/2008 | Yamamichi et al. | 340/426.16 |
| 2008/0133230 A1 | 6/2008 | Herforth | |
| 2008/0238642 A1* | 10/2008 | Mauti | 340/438 |
| 2008/0258890 A1 | 10/2008 | Follmer et al. | |
| 2008/0297336 A1* | 12/2008 | Lee | 340/439 |
| 2009/0096599 A1* | 4/2009 | Kranz | 340/459 |
| 2009/0109037 A1 | 4/2009 | Farmer | |
| 2009/0174572 A1* | 7/2009 | Smith | 340/902 |
| 2009/0256690 A1* | 10/2009 | Golenski | 340/425.5 |
| 2010/0097239 A1* | 4/2010 | Campbell et al. | 340/825.25 |
| 2010/0151838 A1* | 6/2010 | Wormald et al. | 455/414.1 |
| 2010/0156617 A1 | 6/2010 | Nakada et al. | |
| 2011/0063098 A1 | 3/2011 | Fischer et al. | |
| 2011/0063138 A1* | 3/2011 | Berkobin et al. | 340/988 |
| 2011/0065375 A1 | 3/2011 | Bradley | |
| 2011/0140913 A1* | 6/2011 | Montenero | 340/870.07 |
| 2011/0207476 A1* | 8/2011 | Qahwash et al. | 455/456.2 |
| 2011/0304446 A1 | 12/2011 | Basson et al. | |
| 2012/0075118 A1* | 3/2012 | Basir | 340/905 |
| 2012/0126974 A1* | 5/2012 | Phillips et al. | 340/539.13 |
| 2012/0221677 A1* | 8/2012 | Kim et al. | 709/217 |
| 2013/0106618 A1* | 5/2013 | Wormald et al. | 340/905 |
| 2013/0214939 A1* | 8/2013 | Washlow et al. | 340/901 |

OTHER PUBLICATIONS

Office Action dated May 23, 2013 for U.S. Appl. No. 13/603,585.
Office Action dated Oct. 23, 2012 for U.S. Appl. No. 13/004,490.
Final Office Action dated Apr. 30, 2013 for U.S. Appl. No. 13/004,490.
Office Action dated Aug. 1, 2013 for U.S. Appl. No. 13/004,490.
Final Office Action dated Dec. 17, 2013 for U.S. Appl. No. 13/603,585.

* cited by examiner

MOBILE COMPUTING DEVICE EMERGENCY WARNING SYSTEM AND METHOD

RELATED APPLICATION INFORMATION

This application is a Continuation application of co-pending U.S. patent application Ser. No. 13/004,462 filed on Jan. 11, 2011, incorporated herein by reference in its entirety.

This application is related to commonly assigned application: "PREVENTION OF TEXTING WHILE OPERATING A MOTOR VEHICLE", Ser. No. 13/004,490, filed on Jan. 11, 2011 and incorporated herein by reference.

BACKGROUND

1. Technical Field

The present invention relates to mobile devices and communication methods, and more particularly to mobile computing devices configured to work with dynamic networks to warn of events of interest.

2. Description of the Related Art

Mobile computing devices are often installed or used in automobiles or other vehicles. Most of these vehicles contain one or more computers that perform control and monitoring functions of the vehicle's systems and also provide information about conditions or events having to do with the operation of the vehicle.

The mobile computing devices are often underutilized. It would be advantageous to have the additional computing resources in vehicles employed for beneficial uses.

SUMMARY

A warning system and method include a memory device configured to store one or more condition criteria. A monitoring device is configured to monitor a status of the one or more condition criteria. The monitoring device is triggered by a triggering event related to the status to generate a warning signal responsive to the triggering event. A mobile computing device is configured to communicate with the monitoring device and an external network to receive the warning signal and output a warning message on the external network to one or more designated entities.

A warning system includes a vehicle including: a memory device to store one or more condition criteria; a monitoring device configured to monitor a status of the one or more condition criteria, the monitoring device being triggered by a triggering event related to the status to generate a warning signal responsive to the triggering event; and a transceiver configured to communicate with a local network. A mobile computing device is configured to communicate with the vehicle using the local network and to communicate with an external network. The mobile computing device is also configured to receive the warning signal and output a warning message on the external network to one or more designated entities.

A warning notification method includes storing one or more condition criteria in a memory device; monitoring a status of the one or more condition criteria; generating a warning signal responsive to a triggering event related to the status; and using a mobile computing device, communicating between the monitoring device and an external network to receive the warning signal and output a warning message on the external network to one or more designated entities.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
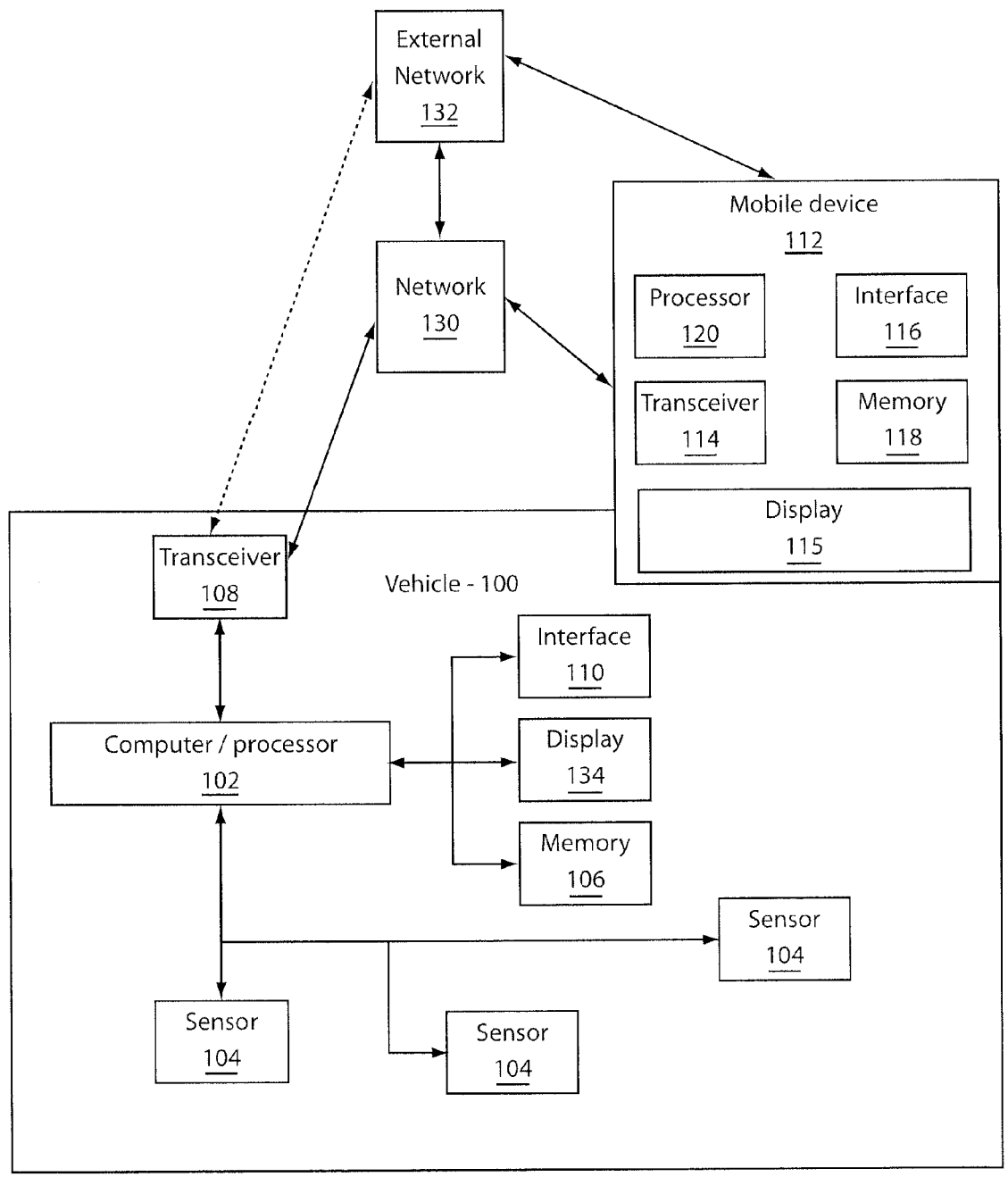
FIG. 1 is a block/flow diagram showing an illustrative warning system in accordance with one exemplary embodiment.

In accordance with the present principles, mobile computing devices, such as a cellular phone, are employed in collaboration with a vehicle's computer to determine when a certain threshold condition has been met or has occurred. When the condition is met, a driver or other subscribed system or systems may be notified via email, wired, or wireless communications of events of interest. Some of these events may include an impending dangerous situation or emergency that has occurred or is about to occur.

The mobile device, in collaboration with the vehicle's sensors, can declare an emergency or unsafe situation. The mobile device may employ information obtained from the vehicle, such as hard braking, radar detection, collision sensors, accelerometers, etc. to determine that an emergency exists or that there is an impending emergency situation. A network may be formed on the basis of connectivity and common interests. The user may set the threshold of the event, the event type, priority, and contact information for various classifications of events. Additionally, those parameters can be set by a designated policy and enforced by a service or a corporate policy. The policy can be enforced using an external service, based upon a vehicle's location, or based upon a corporate policy or local laws. The policy can preferably be dictated by location and/or local governance.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to the drawings in which like numerals represent the same or similar elements and initially to FIG. 1, an illustrative embodiment of a mobile computing device warning system 50 is shown in accordance with the present principles. The system 50 includes a vehicle 100, such as, an automobile, truck, boat, ship, train, plane, tram, etc. The vehicle 100 includes a computer 102 or computing device. Computer 102 may be a standard on-board computer device but may be configured using appropriate hardware and/or software to interact with and communicate with other devices via a network 130. The computer 102 includes a transceiver 108 for carrying out such communications. The computer 102 includes memory 106 for storing policies, user defined event criteria, software for computer 102, software for monitoring sensors 104, software and storage for other functions and applications.

Sensors 104 may include sensors to determine information obtained from the vehicle, such as hard braking, radar detection, collision sensors, accelerometers, etc. Sensors 104 may include sensors to determine if an emergency exists or that there is an impending emergency situation. Sensors 104 may include sensors that monitor a condition of a human within the vehicle. The condition being monitored may be a direct measurement, e.g., measuring a status of a user's pace maker, measuring a drivers position (slumped or sleeping, etc.) or an indirect measurement, e.g., based on system parameters inferring that the driver is unfit to drive.

A local network 130 may be formed on the basis of connectivity and common interests. The user may set the threshold of the event, the event type, priority, and contact information for various classifications of events. Additionally, those parameters can be set by a designated policy and enforced by a service, based on location or based on a corporate or other policy. The policy can be dictated by location and/or local governance. Network 130 may be as simple as providing communication with a mobile device 112, such as cellular telephone, a personal digital assistant, a net book, a computer or other portable device. Network 130 may also include other users, e.g., nearby vehicles, portable devices and the like. The network participants may be determined by a policy or a set of conditions for participation in the network (e.g., proximity, speed, direction, etc.).

Mobile device 112 includes a processor 120, a transceiver 114, a user interface 116 and memory 118. Mobile device 112 and computer 102 are configured to be able to set up a network 130 therebetween to enable communication with each other and with other external networks 132.

It should be understood that the functions described for the vehicle computer 102 may be shared with or carried out by the mobile device 112. A user or a policy mandate describes events of interest based on classification, threshold, and various other criteria. The user criteria and/or policies may be stored in memory 106, memory 118 or at a service provider. The policies may be enforced by a network service provider of the external network 132 and additionally may be affected by or controlled by a context (e.g., speed over 65 miles per hour) or location (e.g., as determined by a global positioning system (GPS)). Based on the classification of such a determination, the mobile device 112 contacts a designated authority or system, such as police, fire, a service truck, or might even notify a spouse.

For example, a minor driver with permission to use a vehicle has the vehicle computer 102 configured to alert a parent by email or other means using the mobile device 112 whenever the vehicle exceeds the speed of 60 miles per hour or goes to an impermissible location. In this instance, a parent may set a user condition using an interface 110 on computer 102, using the interface 116 on the mobile device 112, or by programming the condition through the external network 132 (e.g., using the Internet and a service provider). The computer 102 monitors the speed and/or position of the vehicle using a sensor 104 or using the vehicular devices already in place (speedometer, GPS, etc.). The sensors 104 report the condition or event has occurred to the computer 102, which conveys this information to the mobile device 112 using transceivers 108 and/or 114. The mobile device 112 calls, emails or otherwise notifies the parent or any other individuals on a notification list.

In another aspect, an emergency might be caused by a failing medical device such as a pacemaker. In this instance, sensors 104 may be configured to monitor operations of a pacemaker for a driver. Should a malfunction of the pacemaker occur, the driver and/or any other individual on a notify list may be notified by mobile device 112. The notifications would be sent to the subscribing parties notifying them of the malfunction or other matter. In addition, a position of the vehicle may also be disclosed so that the vehicle may be located by friends and family or emergency personnel.

In another embodiment, the system 50 or components thereof may be configured to interact with other environments. For example, sensing for emergency/critical situations may be performed in stationary environments. For example, if a phone detects a sequence of beeps or other audio sound from a smoke detector in a hotel room or home, the phone can send out a warning of pending fire/heat. The warning may be sent to notify entities on an appropriate notification list.

In another embodiment, the mobile device 112 initiates and/or participates in a social network that permits other mobile users to participate. This allows a mobile device 112, such as a phone, to notify other devices (phones) or interested subscribers of impending problems, such as traffic jams, accidents, or radar traps. It should be understood that this is a dynamic social network, unlike Twitter™. This dynamic social network is preferably an ad-hoc dynamic network that users can join and leave all the time. There may also be an option to join the network without an implicit membership, e.g., in a 'listen only' mode. In such a mode, the user can get updates or information without disclosing any information.

In one embodiment, the social network may include all cars following a particular car at a distance not to exceed, e.g., 0.2 miles, or all phones belonging to health professionals within one mile of a particular phone, or the like. These networks would constantly evolve and would remain silent almost all of the time, consuming few resources.

In one example, the vehicle 100 slows to 5 miles per hour on an interstate with a speed limit of 65 miles per hour. This triggers the computer 102 or the mobile device 112 to search for access for a local network of vehicles on the same interstate within one mile of a position of the vehicle 100. The mobile devices or vehicle computers may have a preselected channel or plurality of channels configured for such communications. Once other devices that meet the criteria are recognized, information may be exchanged. For example, if a vehicle has stalled, the vehicle may output a stalled vehicle indication signal, which can be transmitted in a local area. The indication signal may be received by computer 102 or device 112 and displayed on a display 134 of the vehicle 100 or displayed on a display 115 of the mobile device 112. The message may be further propagated by mobile device 112, may be delivered to entities on a notification list, e.g., by email, text message, etc.

In one embodiment, the transceiver 108 of vehicle 100 may be a cellular transceiver that is built in. For example, the vehicle 100 may conduct cellular communications in the context of a cell phone in the contest of a cellular radio. The transceiver 108 may provide service via satellite as well. In one embodiment, if the vehicle is stolen, the transceiver 108 may be employed to alert a notification list of its location. The location can be determined based on GPS, using cellular location, etc. The request for location may be sent out over the external network 132.

Figure 2:
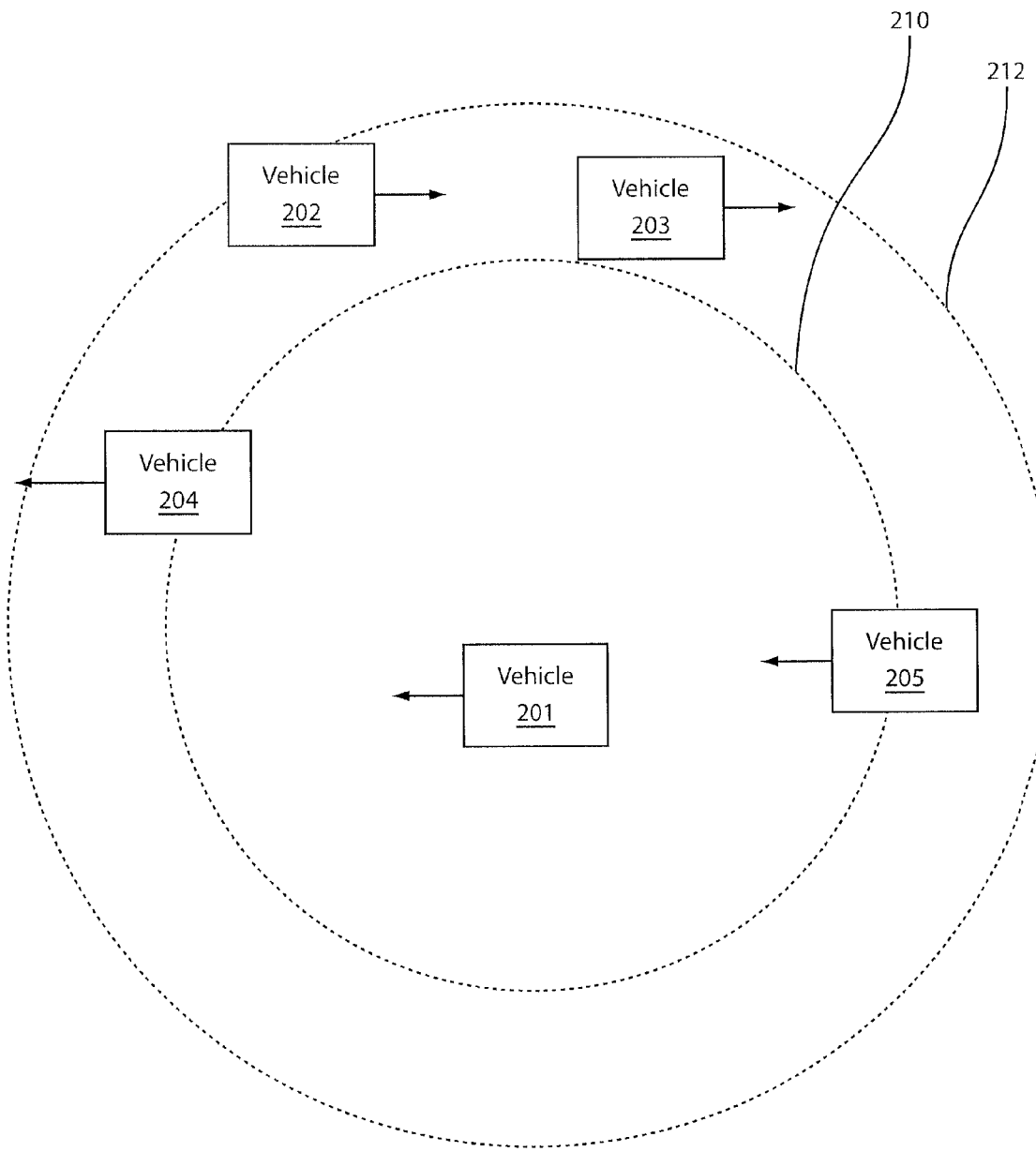
FIG. 2 is a block/flow diagram showing another illustrative warning system in accordance with another exemplary embodiment.

Referring to FIG. 2, an illustrative example of one embodiment is depicted to further demonstrate dynamic networks in accordance with the present principles. In this example, a policy is created that is employed as a traffic warning mechanism. In this example, vehicle 201 is programmed to report traffic to surrounding vehicles within 0.5 miles of a position of vehicle 201. A user may program the 0.5 miles. In addition, the user may configure the reporting criteria and control the manner in which that the warning is reported. A triggering event occurs, the manner and type of which may also be programmed. For example, vehicle 201 has a speed drop below a threshold for a preselected amount of time. The vehicle prompts the user for a report which may be transmitted and recorded verbally, using email, text or any other method. In one instance, the user is prompted to give a verbal report using a mobile device, e.g., with a Blue Tooth™ device or the like. A mobile device is employed to report to other drivers moving in a same direction on the same road that vehicle 201 is positioned on. In one embodiment, the report is received by a service provider (through an external network); the service provider may determine the other vehicles affected by this report and notify them using their respective mobile devices. Since the user has selected a 0.5 mile radius of a circle 210 to inform other drivers, the service provider can locate these drivers within the circle 210 and send a warning to these drivers, e.g., vehicles 204 and 205.

The service provider can determine the positions of other vehicles in the circle 210 using power information or other location systems for the mobile device and/or vehicle computer systems. If GPS information is supported, service provider can further limit the warning to travelers heading in a same direction as vehicle 201 (e.g., vehicles 204 and 205).

Vehicles 202 and 203 may be filtered from receiving the warning message since these vehicles are heading in a different direction. The service provider may employ other filters to ensure that the policies and selections of the users are carried out.

In another scenario, vehicle 201 may be in an accident. Vehicle sensors (104) may generate a signal that the vehicle 201 has been in a collision. The user has selected a 1.0 mile radius of a circle 212 to inform emergency vehicles/personnel of the accident. The service provider of the external network servicing the area can locate emergency personnel within the circle 212 and send a warning and information, e.g., the vehicle's location and the seriousness of the accident. In addition, the emergency personnel can indicate that they are reporting to the scene so that the driver, other drivers and other emergency personnel can employ this information.

Figure 3:
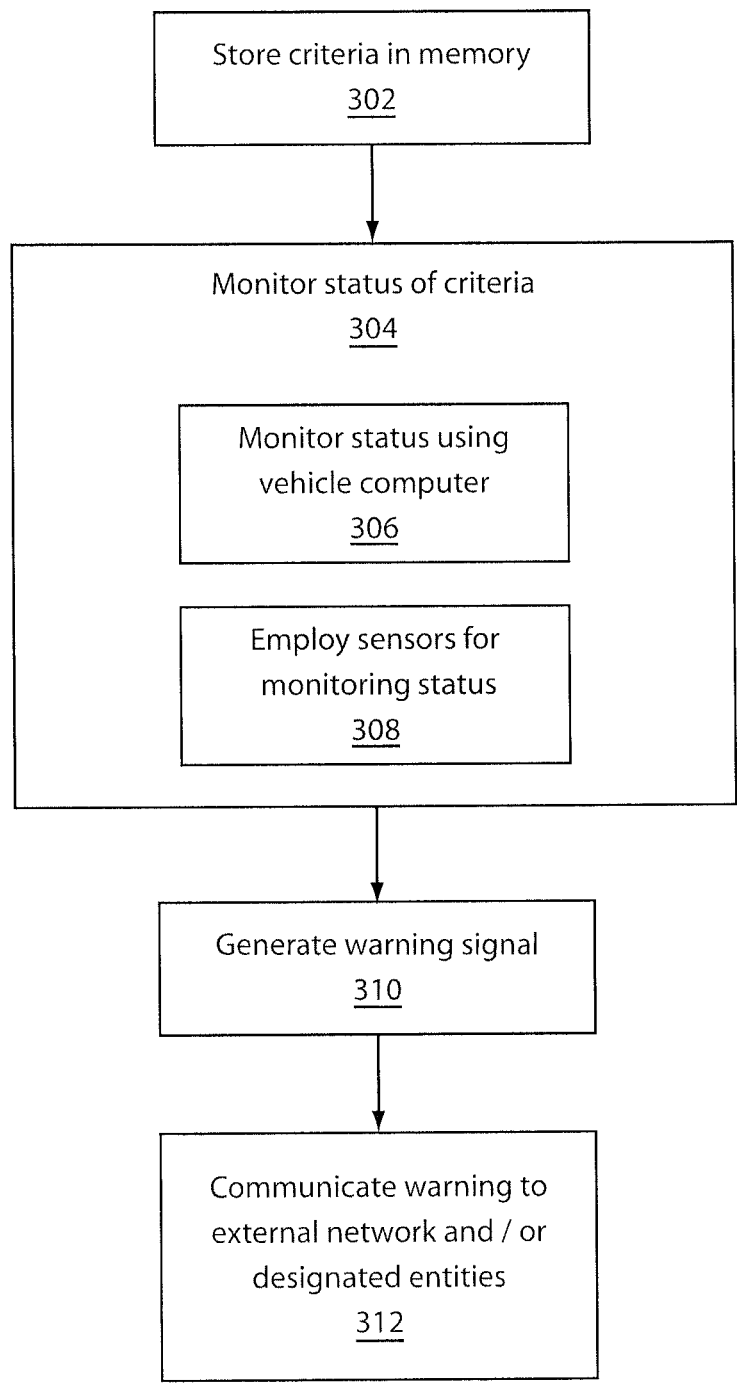
FIG. 3 is a block/flow diagram showing an illustrative warning system/method in accordance with another exemplary embodiment.

Referring to FIG. 3, a warning notification method is shown in accordance with another embodiment. In block 302, one or more condition criteria are stored in a memory device. The criteria may include vehicle status, such as speed, position, fuel amount, engine temperature, etc., accident status and severity, traffic conditions (braking frequency, speed), etc. The criteria may include driver status, e.g., pace maker status, driver position (e.g., slumped/sleeping), etc., passenger status, environmental conditions, or any other criteria. In block 304, a status of the one or more condition criteria is monitored. This may include measuring a parameter and comparing the parameter to a user defined threshold, or comparing newly measured data to old data to determine a change, etc.

In block 306, monitoring the status may include monitoring a vehicle using an on-board computer system. In block 308, monitoring the status may include employing one or more sensors for determining the status of the system. The sensors may be configured to measure at least one of a condition of a vehicle, a condition of a driver of the vehicle and a traffic condition related to the vehicle. Other conditions may also be monitored including those that are not related to the use or status of a vehicle. For example, an emergency event in a hotel or other location.

In block 310, a warning signal is generated responsive to a triggering event related to the status. For example, the triggering event may include exceeding a threshold, determining an accident has occurred, determining a fire or emergency has occurred, etc. In block 312, using a mobile computing device, communication between the monitoring device and an external network may be provided. The communication is enabled so that the mobile computing device receives the warning signal and outputs a warning message on the external network to one or more designated entities.

The mobile computing device includes a wireless communication device and the external network preferably includes a cellular network, although other networks may be employed, e.g., a cable network, home networks, a satellite network, etc. The external network may include one or more service providers that manage system policies. The policies may be employed to limit communications to user designated entities, to control and set up communication links and channels and to provide a way for appropriately distributing warning messages in accordance with user choices.

The designated entities are preferably selected in advance by a user and stored in the memory. These may include the names and contact information for friends, family, medical personnel, other systems, other users, etc. In particularly useful embodiments, the designated entities may include users which achieve user-defined limitations, e.g., other drivers in a 0.2 mile area, northbound travelers on interstate 95, etc.

Having described preferred embodiments for a mobile computing device emergency warning system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A warning system, comprising:
a memory device configured to store condition criteria comprising a driver pace maker status;
a monitoring device configured to monitor a status of the one or more condition criteria, the monitoring device including one or more sensors for monitoring and determining the status of the one or more condition criteria, the monitoring device for measuring a parameter of the driver pace maker status and comparing the parameter to a user-defined threshold, the monitoring device being triggered by a triggering event related to the one or more sensors detecting that the user-defined threshold has been exceeded to automatically generate a warning signal responsive to the triggering event; and
a mobile computing device configured to receive a user-determined radius from a user's vehicle and configured to communicate with the monitoring device and an external network to receive the warning signal and output a warning message via the external network based on the warning signal automatically generated by the monitoring device to one or more designated entities in real-time within a dynamic network comprising the user-determined radius.

2. The system as recited in claim 1, wherein the system is disposed on a vehicle and the monitoring device and the memory device are part of an on-board computer system.

3. The system as recited in claim 1, wherein the one or more sensors are configured to measure at least one of a condition of a vehicle, a condition of a driver of the vehicle and a traffic condition related to the vehicle.

4. The system as recited in claim 1, wherein the mobile computing device includes a wireless communication device and the external network includes a cellular network.

5. The system as recited in claim 1, wherein the designated entities are selected in advance by a user and stored in the memory device.

6. The system as recited in claim 1, wherein the designated entities include one or more of emergency personnel, a personal contact and other users.

7. The system as recited in claim 1, wherein the designated entities include users which achieve user-defined limitations.

8. A warning system, comprising:
a vehicle including:
a memory device to store configured to store condition criteria comprising a driver pace maker status;
a monitoring device including one or more sensors configured to monitor a status of the one or more condition criteria, the monitoring device for measuring a parameter of the driver pace maker status and comparing the parameter to a user-defined threshold, the monitoring device being triggered by a triggering event related to the one or more sensors detecting that the user-defined threshold has been exceeded to automatically generate a warning signal responsive to the triggering event;

a transceiver configured to communicate with a local network; and a mobile computing device configured to receive a user-determined radius from a user's vehicle and configured to communicate with the vehicle using the local network and to communicate with an external network, the mobile computing device configured to receive the warning signal and output a warning message via the external network based on the warning signal automatically generated by the monitoring device to one or more designated entities including entities in real-time within a dynamic network comprising the user-determined radius.

9. The system as recited in claim 8, wherein the vehicle includes an interface to permit user determined parameters to be monitored.

10. The system as recited in claim 8, wherein the one or more sensors for determining the status of the system are configured to measure at least one of a condition of the vehicle, a condition of a driver of the vehicle and a traffic condition related to the vehicle.

11. The system as recited in claim 8, wherein the mobile computing device includes a wireless communication device and the external network includes a cellular network.

12. The system as recited in claim 8, wherein the designated entities are selected in advance by a user and stored in the memory device.

13. The system as recited in claim 8, wherein the designated entities include one or more of emergency personnel, a personal contact and other users.

14. The system as recited in claim 8, wherein the designated entities include users which achieve user-defined limitations.

15. The system as recited in claim 8, wherein the external network includes a service provider that manages policies to limit communications to the user designated entities.

16. A computer readable storage medium comprising a computer readable program, wherein the computer readable program when executed on a computer causes the computer to perform the steps of:

storing condition criteria comprising a driver pace maker status in a memory device;

monitoring a status of the driver pace maker status;

measuring a parameter of the driver pace maker status and comparing the parameter to a user-defined threshold;

receiving a user-determined radius;

detecting that the user-defined threshold for the parameter of the one or more condition criteria has been exceeded;

automatically generating a warning signal responsive to a triggering event comprising wherein the user-defined threshold is exceeded; and enabling communication to an external network to receive the warning signal and to output a warning message via the external network based on the warning signal automatically generated by the monitoring device to one or more designated entities in real-time within a real-time dynamic network comprising the user-determined radius.

17. The computer readable storage medium as recited in claim 16, further comprising a mobile computing device to enable the communication to the external network.

18. The system as recited in claim 1, wherein the one or more sensors monitor operation of a medical device for a driver of a vehicle.

19. The system of claim 18, wherein if a malfunction in the medical device occurs, the mobile device notifies at least one of the driver or an individual on a notify list.

* * * * *